United States Patent [19]

Silversides et al.

[11] Patent Number: 4,879,112
[45] Date of Patent: * Nov. 7, 1989

[54] MONOCLONAL ANTIBODIES AGAISNT GNRH

[75] Inventors: David W. Silversides; Reuben J. Mapletoft; Bruce D. Murphy; Virkam Misra, all of Saskatoon, Canada

[73] Assignee: University of Saskatchewan, Saskatoon, Canada

[*] Notice: The portion of the term of this patent subsequent to Jun. 30, 2004 has been disclaimed.

[21] Appl. No.: 50,023

[22] Filed: May 15, 1987

Related U.S. Application Data

[63] Continuation of Ser. No. 577,694, Feb. 7, 1984, Pat. No. 4,676,981.

[51] Int. Cl.$^4$ .................... A61K 39/395; C12N 5/00; C12N 15/00; C12P 21/00
[52] U.S. Cl. .................................. 424/85.9; 530/387; 435/68; 435/240.27; 435/172.2; 935/104; 935/107
[58] Field of Search ................. 435/68, 172.2, 240.27, 435/948; 935/93, 95, 104, 107; 424/85, 85.9; 436/548; 530/387

[56] References Cited

U.S. PATENT DOCUMENTS

4,676,981 6/1987 Silversides et al. .................. 435/68

OTHER PUBLICATIONS

Talwar et al, 2nd Int. Conference on Immunopharmacology ed, Hadden et al, Jun. 1983, pp. 415–420.
Arimura, A., L. Debeljuk, and A. V. Schally, Endocrinology 95: 323, 1974.
McCormack et al, Endocrinology, 100(3), pp. 633–667 (1977).
Shastri et al, Am. J. Reprod. Immunol. 1, pp. 262–265 (1981).
Siddle et al, Monoclonal Antibodies and Developments in Immunoassay, ed. Albertini (1981), pp. 53–66.
Lincoln et al, J. Reprod. Fert. 66, pp. 703–708 (1982).
Koch, Y. P. Chobsieng, U. Zor, M. Fridkin, and H. R. Lindner, Biochem Biophys Res. Commun 55: 623, 1973.
Kerdelhue, B., S. Catin, and M. Jutisz, In Motta, M., P. G. Crosignani, and L. Martini (eds.), Hypothalmic Hormones, Academic Press, London, 1975, p. 49.

Primary Examiner—John E. Tarcza
Attorney, Agent, or Firm—Bachman & LaPointe

[57] ABSTRACT

A monoclonal antibody against GnRH and particularly designated USASK/DSIL-GnRH is produced by a hybrid formed by fusion of cells from a myeloma line and antibody producing cells of the immune system from an animal previously immunized with a source of GnRH; the monoclonal antibody has the following characteristics:
  (i) it produces a short term reduced mean level of luteinizing hormone (LH) in immunized mammals;
  (ii) it produces a short term reduced pulsatile secretion of LH in immunized mammals;
  (iii) it terminates pregnancy in a female mammal with an accompanying decline in progesterone levels;
  (iv) it produces a long term reduced testosterone level in a male mammal, and,
  (v) it induces inferility in a male mammal;

thus passive immunization of the female or male with the monoclonal antibodies may be employed to reduce fertility and terminate pregnancy.

21 Claims, 13 Drawing Sheets

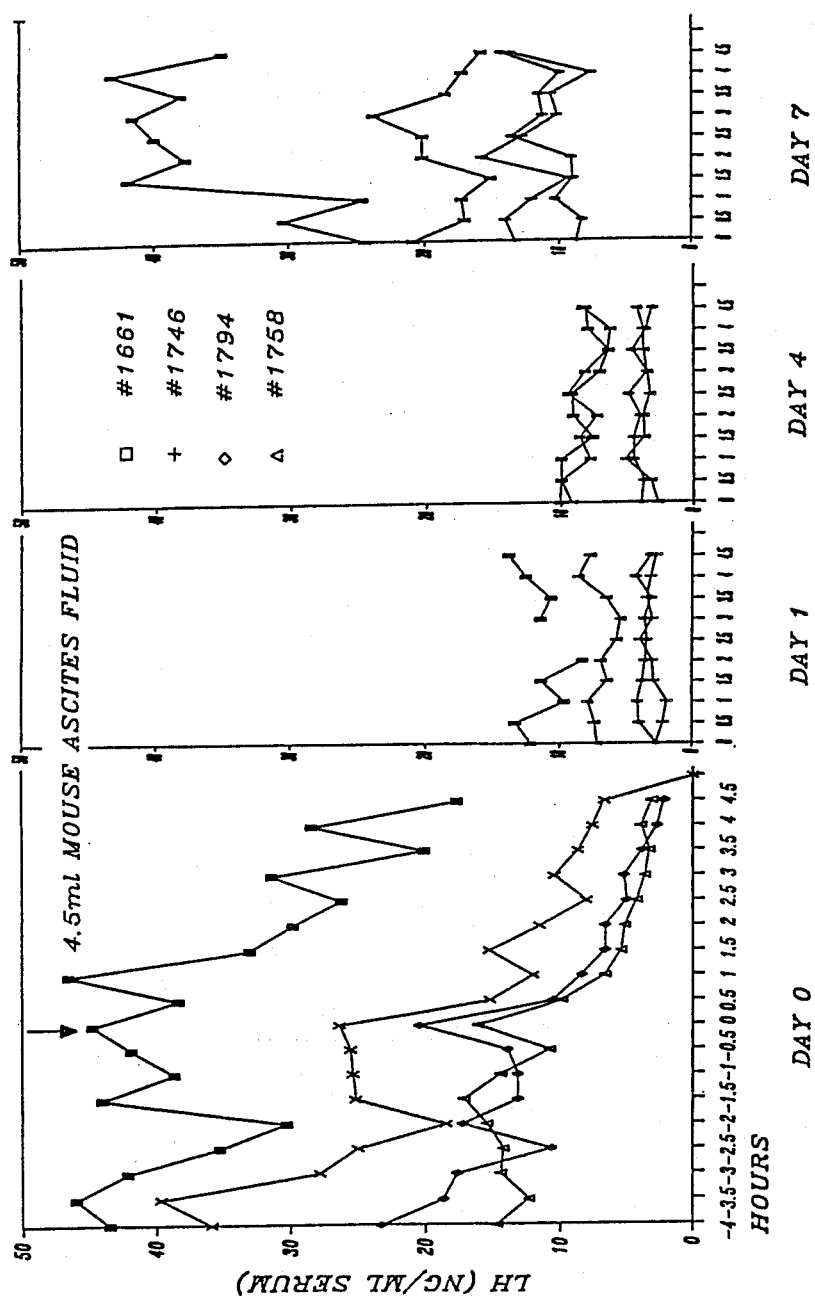

FIG.7(a). *FEMALE DOG PASSIVE INFUSION WITH GnRH ANTIBODIES*
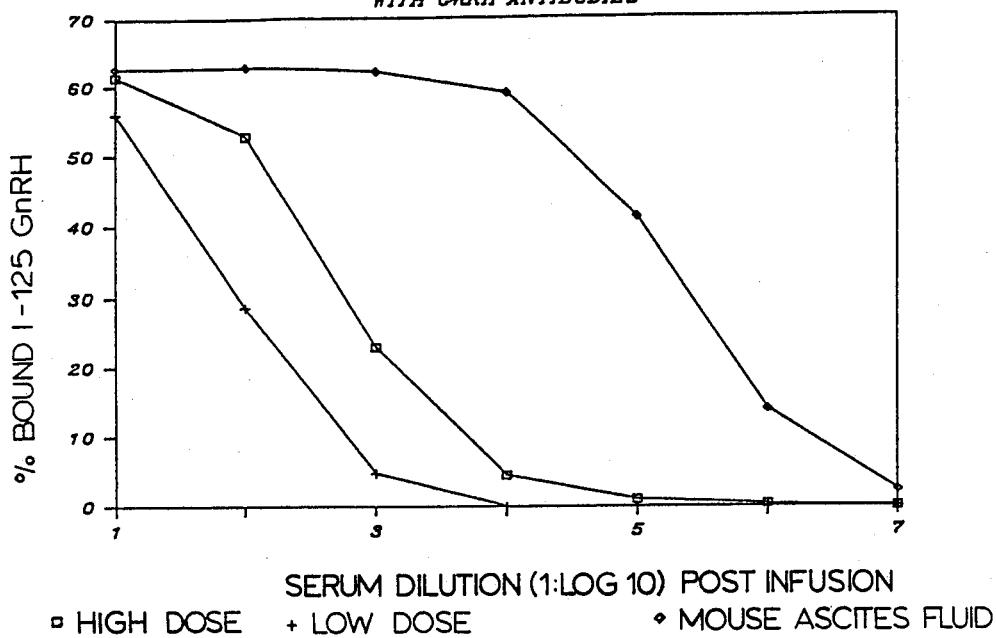
SERUM DILUTION (1:LOG 10) POST INFUSION
□ HIGH DOSE     + LOW DOSE     ◇ MOUSE ASCITES FLUID
FIG.7(b). *FEMALE DOG PASSIVE INFUSION WITH GnRH ANTIBODIES*
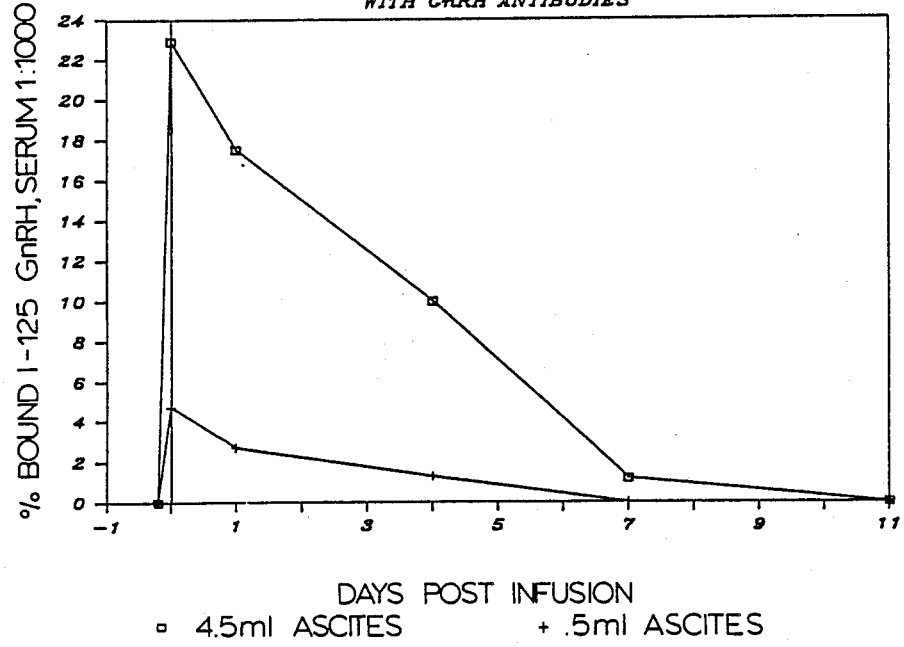
DAYS POST INFUSION
□ 4.5ml ASCITES     + .5ml ASCITES

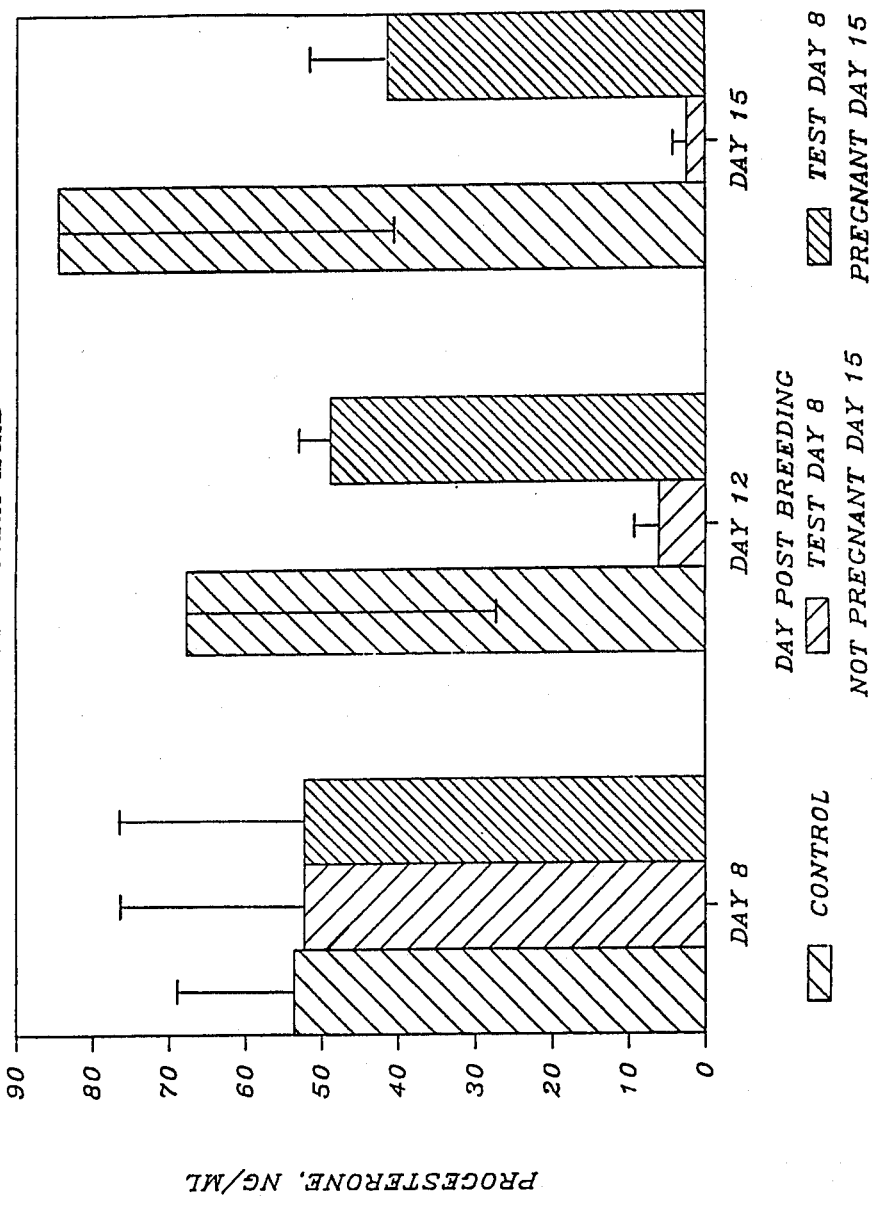
FIG. 8(b). FEMALE RAT PASSIVE IMMUNIZATION WITH GnRH MoAB

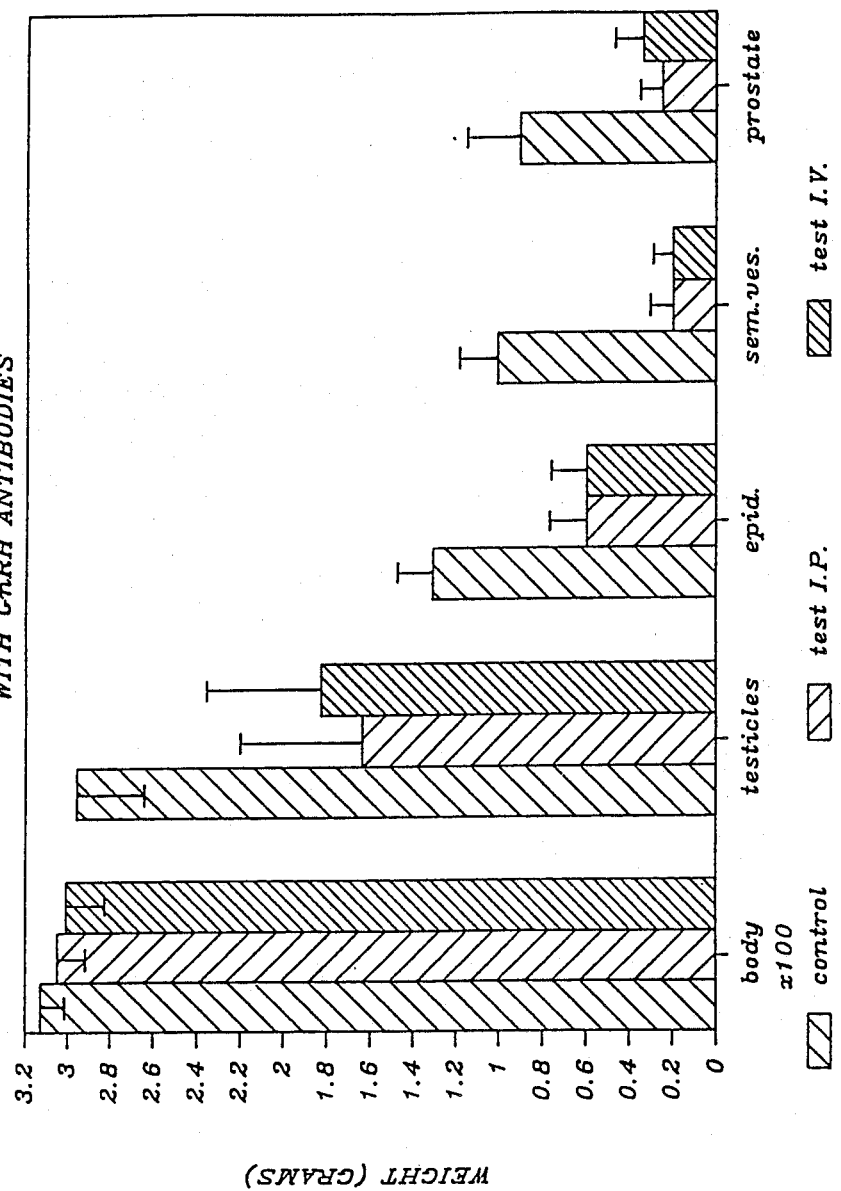
FIG. 10. MALE RAT PASSIVE INFUSION WITH GnRH ANTIBODIES

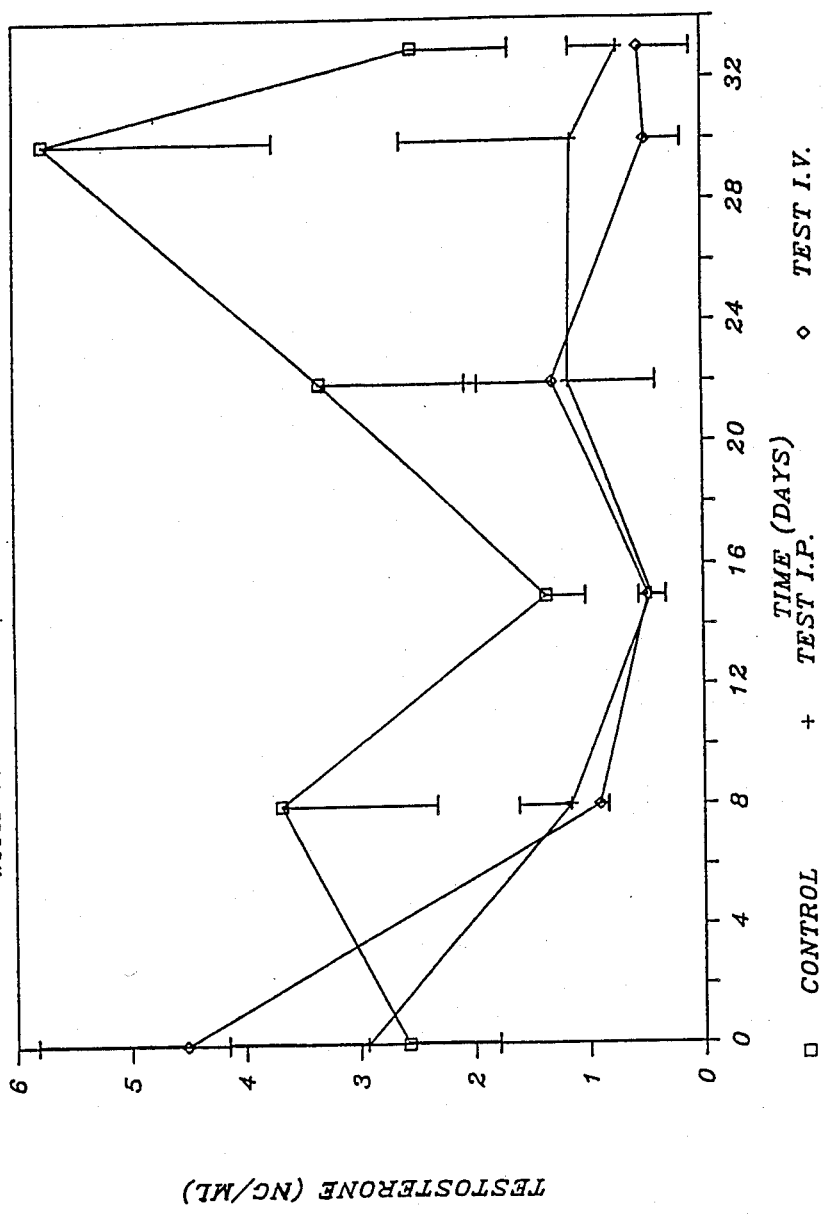

MONOCLONAL ANTIBODIES AGAISNT GNRH

CROSS REFERENCE TO RELATED APPLICATIONS

This application is a continuation of U.S. patent application Ser. No. 577,694, filed Feb. 7, 1984, now U.S. Pat. No. 4,676,981.

BACKGROUND OF THE INVENTION (i) Field of the Invention

This invention relates generally to new monoclonal antibodies and their preparation and use, as well as to a new hybridoma for the harvesting of the monoclonal antibodies and its method of production.

(ii) Description of the Prior Art

Antibodies are protein molecules found in vertebrates and are involved in the defense of the organism against foreign invasion. Antibodies are unique in that they bind with exquisite specificity to the molecule they were generated against. The mammalian immune system has the capacity to generate antibodies against virtually any organic molecule. Monoclonal antibody technology permits the identification and indefinite growth of cells that produce a single species of antibody which binds to a molecule of choice. This enables the production of virtually an unlimited amount of specific antibody directed against virtually any molecule of biological interest.

Monoclonal antibodies having a definite antigen binding specificity may be produced employing the hybridoma technique developed by Kohler and Milstein (Nature 256, 495–497, 1975), or modifications thereof.

While the concept of the technique of producing monoclonal antibodies from hybridomas is understood, there are many difficulties met and variations required for each specific case.

Indeed, there is no assurance, prior to attempting the preparation of a particular hybridoma, that the hybridoma will be obtained, that the hybridoma will produce an antibody, or that any antibody so produced will have the desired specificity.

The functional integrity of the mammalian reproductive system is dependent on the correct levels and interplay of the various sex hormones. Key among these hormones is a small polypeptide produced in the hypothalamus of the brain. This polypeptide, termed GnRH, (Gonadotropic Releasing Hormone) also known as LHRH (Luteinizing Hormone Releasing Hormone) is released into the blood and is active on the pituitary gland. (Schally, A. V., A. Arimura, A. J. Kastin (1973). "Hypothalamic regulating hormones." Science 179:341-350.) Here it effects the release of two protein sex hormones, the gonadotropins Luteinizing Hormone (LH) and the Follice Stimulating Hormone (FSH). These two hormones then act in concert on the gonads, namely the ovaries in females and the testes in males, to produce normal development of egg cells or sperm. In addition LH induces ovulation in the female. Thus it is seen that GnRH is required in general for the maintenance of reproductive functions in both male and female, and also on an acute basis for cyclicity in females.

Immunological neutralization of GnRH is an effective way to block the normal patterns of GnRH release and thus to effect reproductive functions. This has been shown in laboratory animals and domestic species after active and passive immunization against GnRH. (Arimura, A., C. Debeljuk, A. V. Schally (1974). "Blockade of the Preovulatory Surge of LH and FSH and of Ovulation by anti-LH-RH Serum in Rats." Endo 95:323-325; McCormack, J. T., T. M. Plant, D. L. Hess, E. Knobil (1977). "The Effect of Luteinizing Hormone Releasing Hormone (LHRH) Antiserum Administration of Gonadotropin Secretion in the Rhesus Monkey." Endo 100:663-667; Jeffcoate, I. A., J. P. Foster, D. B. Crighton (1978). "Effect of Active Immunization of Ewes Against Synthetic Luteinizing Hormone Releasing Hormone." Therio 10:323-325; and Schanbacher, B. D. (1982). "Responses of Ram Lambs to Active Immunization Against Testosterone and Luteinizing Hormone-Releasing Hormone." Am. J. Physio. 242(3), E201-5.)

SUMMARY OF THE INVENTION

It is an object of the invention to provide monoclonal antibodies having a specificity for GnRH.

It is a further object of this invention to provide a process for producing monoclonal antibodies having a specificity for GnRH.

It is a still further object of this invention to provide a new hybridoma, and method of producing such hybridoma for the production of monoclonal antibodies having a specificity for GnRH.

In accordance with the present invention it has been found that passive immunization of the female mammal with monoclonal antibodies against GnRH results in reduced mean LH levels and reduction in pulsatile secretions of LH for a period following such immunization.

It has also been found that administration of monoclonal antibodies against GnRH to a pregnant female mammal is effective in terminating the pregnancy, such termination being accompanied by a marked decline in progesterone secretion by the ovary.

Long term maintenance of the circulatory titer of monoclonal antibodies against GnRH in male mammals produced significant effects on breeding ability, sex gland weight and morphology as well as on the testosterone levels. In particular, testosterone levels in test animals were reduced significantly as compared with control animals.

Thus, in accordance with one aspect of the invention, there is provided a monoclonal antibody produced by a hybrid formed by fusion of cells from a myeloma line and antibody-producing cells of the immune system from an animal previously immunized with a source of GnRH.

In particular the myeloma line may be a mouse myeloma line, however, myeloma lines from other mammals including humans may also be employed. The myeloma line is most suitably one which does not induce antibody formation in an animal of the class in which it originates. The antibody-producing cells may be cells from the immune system, for example, spleen, lymph nodes, as well as white blood cells; the spleen cells are generally preferred.

Preferably the myeloma line and the antibody-producing cells are from the same class of animal.

Thus in particular the monoclonal antibody may be produced by a hybridoma formed by fusion of cells from a mouse myeloma line and spleen cells from a mouse previously immunized with a source of GnRH.

In another aspect of the invention there is provided a hybridoma formed by fusion of cells from a mouse myeloma line and spleen cells from a mouse previously immunized with a source of GnRH.

In yet another aspect of the invention there is provided a method of producing a hybridoma comprising fusion of cells from a mouse myeloma line and spleen cells from a mouse previously immunized with a source of GnRH.

In yet another aspect of the invention there is provided a process for producing monoclonal antibodies to GnRH comprising: (a) immunization of an animal with a source of GnRH, (b) removal of antibody-producing cells of the immune system from said immunized animal and forming a suspension of the cells, (c) fusion of the cells with a myeloma cell line; (d) dilution and culture of the cells from (c) comprising hybrid cells and unfused cells in separate wells in a medium which will not support the unfused cells, (e) evaluation of the supernatant in the wells containing hybrid cells for the presence of antibody demonstrating a specificity to GnRH; and (f) cloning of a selected hybrid from (e).

In a particular embodiment step (a) comprises immunizing a mouse with a source of GnRH, step (b) comprises removing the spleen from the immunized mouse, and step (c) comprises fusing the spleen cells with a mouse myeloma line to produce hybridomas.

In a further aspect of the invention there is provided a method for terminating pregnancy in a female mammal comprising administering to a pregnant female mammal an effective amount of a monoclonal antibody against GnRH, of the invention.

In still a further aspect of the invention there is provided a method for preventing ovulation in a female mammal comprising administering to said mammal an effective amount of a monoclonal antibody against GnRH of the invention.

In yet a further aspect of the invention there is provided a method for reducing testosterone levels in a male mammal comprising administering to said mammal an effective amount of a monoclonal antibody against GnRH of the invention.

In yet another aspect of the invention there is provided a method for inducing infertility in a male mammal comprising administering to said mammal an effective amount of a monoclonal antibody against GnRH, of the invention.

DETAILED DESCRIPTION OF THE INVENTION

Hybridoma Production

The method of preparing the hybridoma may, in particular, comprise the general steps of:
(a) immunizing Balb/c mice with a source of GnRH,
(b) removing the spleens from the immunized mice and forming a suspension of spleen cells,
(c) fusing the suspended spleen cells with mouse myeloma cells from a cell line with a fusion promoter,
(d) diluting and culturing the mixture of fused and unfused cells from (c) in separate wells in a culture medium which will not support the unfused cells; this allows the unfused cells to die,
(e) evaluating the supernatant in each well containing a hybridoma for the presence of antibody to GnRH, and
(f) selecting hybridomas producing the desired antibody for further culturing.

Any source of GnRH may be employed for production of the hybridomas, including purified GnRH.

In particular since GnRH is a hapten it is employed in a conjugated form, bound to a carrier molecule. As the carrier molecule there may be employed a protein, for example, bovine serum albumin or keyhole limpet hemocyanin.

Several mouse myeloma cell lines are known and available, one such cell line is that designated P3-NS1/1-Ag4-1 and is on deposit with the American Culture Collection under Accession Number ATCC T1B18.

As the fusion promoter there may suitably be employed polyethylene glycol having a molecular weight of about 1,000.

After the fusion it is necessary to isolate the fused cells or hybridomas from the heterogenous mixture of fused and unfused cells.

The non-fused lymphocytes of the spleen have a short natural life and will die naturally after a few days in the culture. The main task is to eliminate the unfused myeloma cells. This can be achieved, for example, by use of a HAT selection medium, a technique which is well known and has been described, for example, by Littlefield in Science, 145, 709-710, 1964. This technique requires that the myeloma cell line be of a type which will not survive in HAT selection medium, for example, by virtue of its lacking an enzyme such as thymidine kinase (TK) or hypoxanthine-guanine phosphoribosyl transferase (HGPRT). In the fused cells the enzyme is provided by the lymphocyte component of the fusion.

Monoclonal Antibody Production

The monoclonal antibodies may be produced from the selected hybridomas by two routes:
(i) In vitro culturing of a selected hybridoma in a suitable culture medium for an appropriate length of time and recovery of antibody from the culture supernatant,
(ii) injection of a selected hybridoma into mice to permit the formation of antibody-producing ascites tumors, and harvesting the desired antibody from the blood and ascites fluid of the mice.

The latter technique is the more practicable since greater quantities of antibody can be produced, although the resulting antibody is less pure since normal antibodies of the mice may also be present.

Although preparation of the monoclonal antibodies has been particularly described by reference to hybridomas formed by fusion of a mouse myeloma line and spleen cells, it will be evident that hybrids of other myeloma cells and antibody-producing cells of the immune system will also provide an appropriate source of the antibodies.

Characterization of Monoclonal Antibodies

The selected monoclonal antibody is designated USASK/DSIL-GnRH and is derived from the hybridoma designated by USASK/DSIL-LHRH-A1 deposited in ATCC (American Type Culture Collection), Rockville, Md., U.S.A., and having ATCC Designation HB-9094.

USASK/DSIL-GnRH is characterized in that it will terminate pregnancy in a female mammal, with a corresponding decline in progesterone levels.

Tests showed that a minimum dosage of USASK/DSIL-GnRH is necessary, and also that, depending on the species, the day of pregnancy at administration is a factor.

Tests also showed that pregnancy was not terminated under comparable conditions, in cases in which the pregnant animal was fitted with a progesterone implant capable of maintaining a level of progesterone characteristic of pregnancy.

USASK/DSIL-GnRH is further characterized in that it produces a long term reduced testosterone level in male mammals.

In tests on male rats, maintenance of USASK/DSIL-GnRH at titers found to bind above 30% of radioactive labelled GnRH, 1:1000 serum dilution in vitro, for 30 days produced a substantial lowering of testosterone levels. Levels below 2 ng/ml were maintained from day 8 to day 30 in test rats, as compared with levels ranging widely from about 1.5 to about 6 ng/ml in the control rats over the same period.

USASK/DSIL-GnRH may also be characterized as producing a short term reduction in mean level of gonadotropin Luteinizing Hormone (LH) as well as short term reduced pulsatile secretion of LH, when administered to a mammal.

In particular, dogs immunized with pooled mouse ascites fluid containing USASK/DSIL-GnRH exhibited a reduction in the mean level circulation of LH and in pulsatile secretions of LH for up to 4 days after immunization.

Tests showed that a minimum dosage of USASK/DSIL-GnRH was necessary to produce such reduction, which minimum dosage can be readily determined by experiment.

By way of example, dogs immunized with 4.5 ml of the pooled mouse ascites fluid displayed the reduced mean LH levels and the reduced pulsatile secretion of LH for up to 4 days, whereas these levels were unaffected in dogs immunized with a lower dosage of only 0.5 ml of the pooled ascites fluid.

Optical density readings by ELISA* indicate that the antibody allotype of USASK/DSIL-GnRH is mouse IgG1 and thus has a $\gamma_1$ (gamma) heavy chain, a molecular weight of about 180,000 Daltons and one basic 4-peptide unit.
*enzyme linked immunosorbant assay system In a primary binding assay USASK/DSIL-GnRH raised as an ascites fluid tumor in the peritoneal cavity of BALB/c mice bound more than 30% of an $I^{125}$ GnRH at $1:4\times10^5$ dilution of ascites fluid.

In a competitive binding assay USASK/DSIL-GnRH raised as an ascites fluid tumor in the peritoneal cavity of BALB/c mice, and diluted at from $1:4\times10^5$ to $2\times10^6$ was used as the basis of a competitive inhibition assay in conjunction with $I^{125}$ GnRH. In this way the binding of USASK/DSIL-GnRH to unlabelled GnRH and various GnRH analogues and other hormones was characterized:

(a) Unlabelled GnRH produces 50% inhibition at 30 ng/ml,
(b) Salmon GnRH (Leu6-Trp7) produces 50% inhibition at 2.6 µg/ml, (i.e. relative activity is 1% of native unlabelled GnRH),
(c) 6-D-Leu GnRH produces 50% inhibition at 100 µg/ml (i.e. relative activity is 0.03% of native unlabelled GnRH),
(d) Thyroid Releasing Hormone (TRH) produces about 50% inhibition at about 10 mg/ml (i.e. relative activity is about 0.0001% of native unlabelled GnRH),
(e) LH demonstrated no competitive inhibition,
(f) FSH demonstrated no competitive inhibition.

The aforementioned ascites fluid was recovered from 100 mice injected with $5\times10^4$ to $1\times10^6$ cells (hybridoma) an average of 4 ml of ascites fluid being collected per mouse (range 0.5 to 12 ml).

The dose of the ascites fluid containing USASK/DSIL-GnRH, required to terminate pregnancy in 50% of female rats treated on day 9 of pregnancy was 0.1 ml per 250 gm body weight, i.e. 0.4 ml/kg. Thus a 0.8 ml/kg dose represents a 100% effective dose.

A minimum titer of 10% binding at $1:1\times10^3$ serum dilution from dog blood was still effective in reducing LH levels in female spayed dogs, 4 days after ascites fluid injection.

MATERIALS AND METHODS

Iodination of GnRH

Iodinated GnRH, used in subsequent primary binding screening assays and competitive binding assays, was produced by a modification of the chloramine-T method. To 2.5 µg GnRH (Factrel, trade mark of Ayerst, McKenna & Harrison) in 2.5 µl distilled water was added 25 µl of 0.5 M phosphate buffer, pH 7.5. One mCi of $I^{125}$ in a volume of 10 µl was then added to the reaction vial followed by 40 µl of Chloramine-T solution (0.5 mg Chloranine-T in 1 ml 0.05 M phosphate buffer). The reaction was allowed to proceed for 15 seconds and then terminated by the addition of 100 µg sodium metabisulfite in 50 µl 0.05 M phosphate buffer. Iodinated GnRH was then separated from free iodine by using an 11 ml column of Sephadex G-25, (trade mark for synthetic beads derived from polysaccharide dextran - Pharmacia Fine Chemicals Inc.). Characteristically the labelled GnRH was eluted as the second radioactive peak, following the free iodine.

Primary Binding Assay for GnRH Antibodies

Iodinated GnRH was used in the development of a primary binding assay for the detection of GnRH antibodies and measurement of GnRH Antibody titer. Serum samples (0.1 ml) or culture solution (0.1 ml) were incubated in $12\times75$ borosilicate test tubes in the presence of 0.1 ml $I^{125}$ labelled GnRH, diluted in phosphate buffered saline (PBS), 0.1% gelatin to approximately 20,000 counts per minute per 0.1 ml. After overnight incubation at 4° C., 1 ml of cold ethanol was added to separate bound from free labelled GnRH. The tubes were subjected to centrifugation and the precipitate was counted in a Micromedic automated gamma counter. Total counts and nonspecific binding of label were determined. Serial dilutions of biological solutions were made for titer determinations.

Conjugation of GnRH to Carrier Molecules

In a typical conjugation procedure, 500 µg GnRH (Factrel) was added to 500 µg carrier protein (bovine serum albumin, from Sigma Chemicals, or keyhole limpet hemocyanin from Sigma Chemicals) in 0.9 ml distilled water. To this mixture was added 20 mg carbodiimide (Sigma Chemicals) in 100 µl distilled water. The reaction was allowed to proceed at room temperature overnight, whereupon the mixture was dialyzed against cold distilled water for 24 hours. The dialyzed material was either used immediately or lyophilized and stored for future use.

BRIEF DESCRIPTION OF THE DRAWINGS

*
In FIGS. 2 and 3 B/B(O) refers to:

$$\frac{\text{binding of radioactively labelled hormone at } (X) \text{ concentration of unlabelled hormone}}{\text{binding of radioactively labelled hormone at zero concentration of unlabelled hormone}}$$

where X is some concentration greater than zero. Thus B/B(O) is one form of expressing competitive inhibition assay data.

Figure 4:
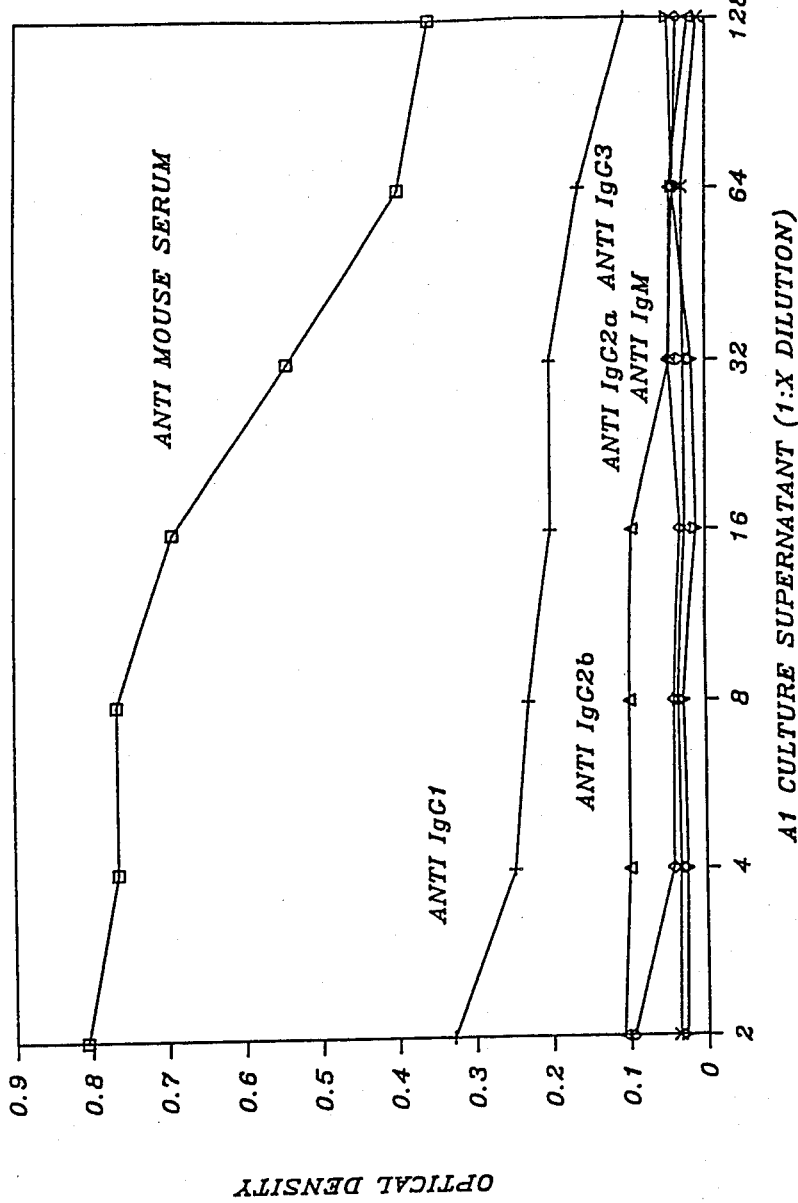

FIG. 4 shows graphically the results of an enzyme linked immunoabsorbant assay (ELISA) for allotype determination of USASK/DSIL-GnRH;

FIG. 5 depicts graphically LH levels of dogs immunized with 4.5 ml pooled mouse ascites fluid containing USASK/DSIL-GnRH;

FIG. 6 depicts graphically LH levels of dogs immunized with 0.5 ml pooled mouse ascites fluid containing USASK/DSIL-GnRH;

FIGS. 7A and 7B show graphically the mean titers of USASK/DSIL-GnRH in serial dilutions of dog sera immediately post immunization, and mean titers at 1:1000 serum dilution over time, respectively.

Figure 8A:
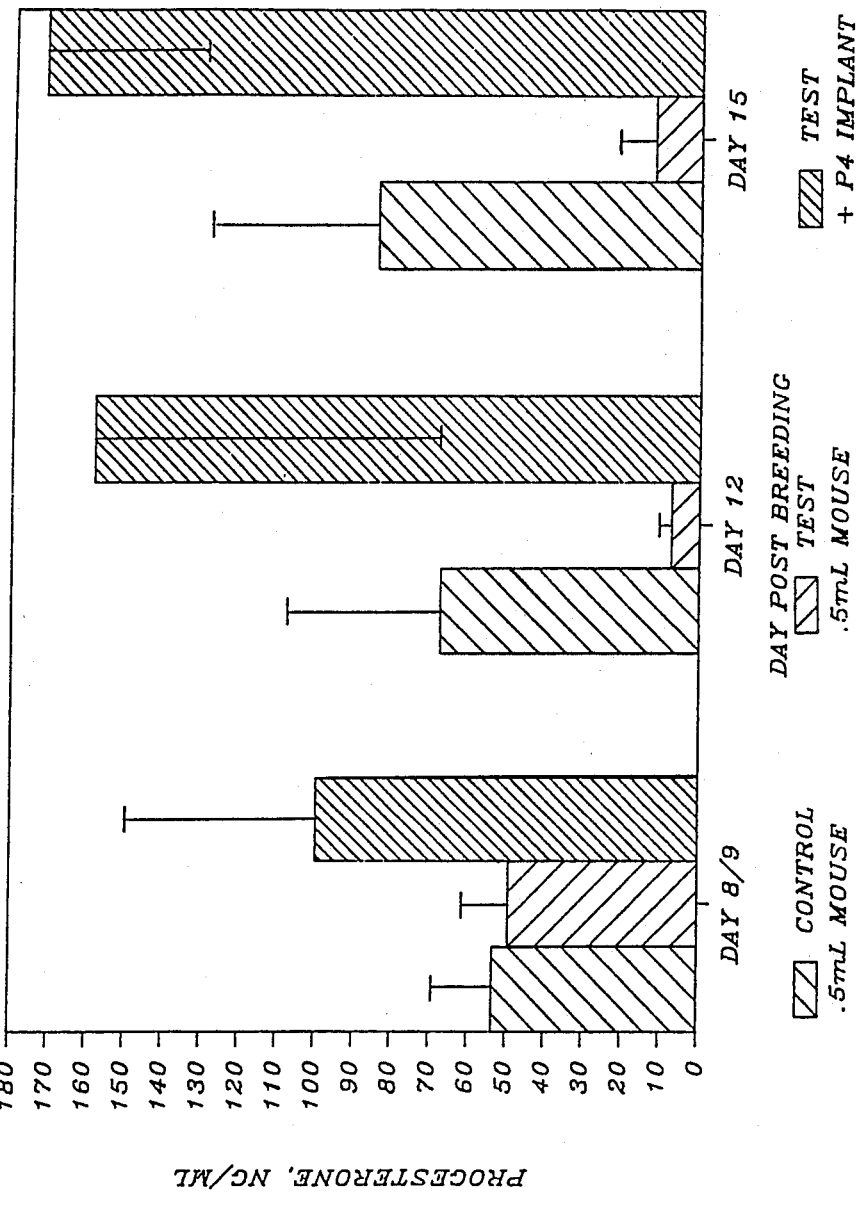
Figure 9:
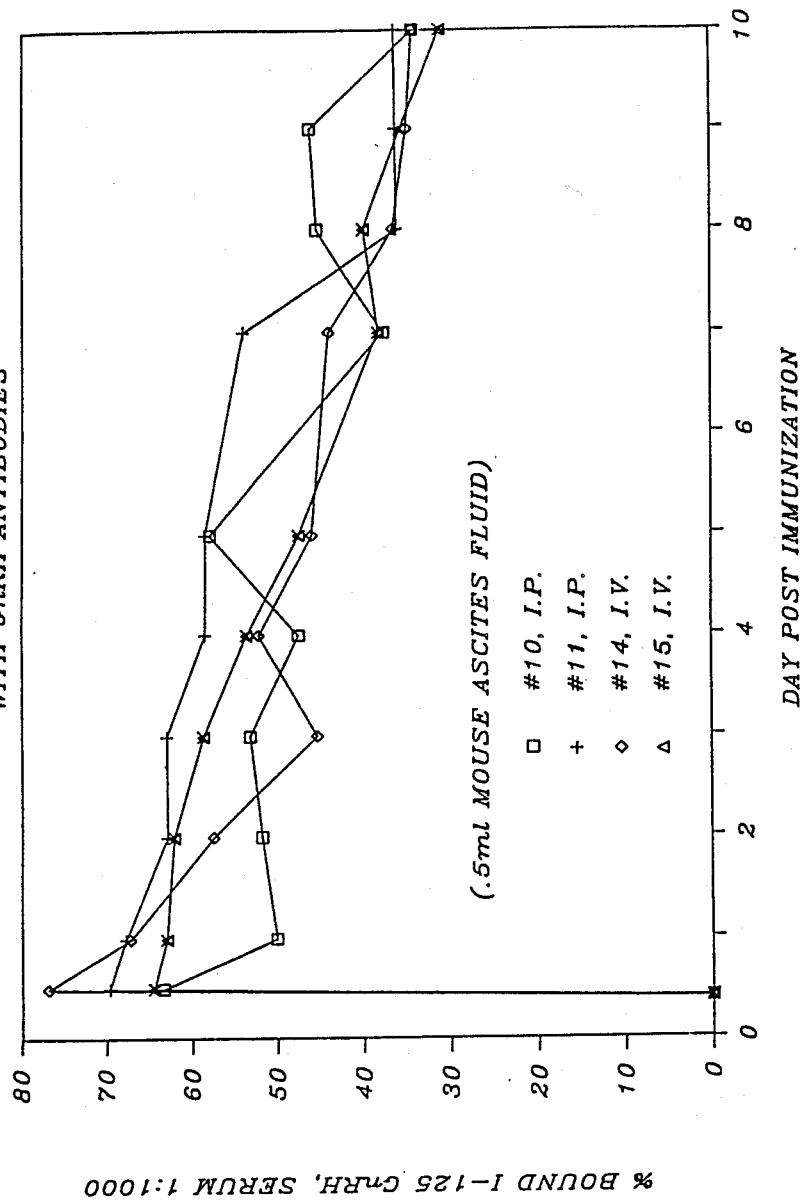

FIGS. 8A and 8B show progesterone values at different stages of pregnancy for control mice, test mice having an intravenous injection of 0.5 ml ascites fluid containing USASK/DSIL-GnRH, and mice having the same intravenous injection but having a progesterone implant;

FIG. 9 shows graphically the titer against $I^{125}$ GnRH for USASK/DSIL-GnRH administered by i.p. and i.v. routes;

FIG. 10 demonstrates the reduction in weights of testicles, epididymides, seminal vesicles and prostate glands in control animals and in test animals treated with USASK/DSIL-GnRH; and FIG. 11 illustrates graphically testosterone levels in control animals and in test animals treated with USASK/DSIL-GnRH.

EXAMPLES

EXAMPLE 1

Production of Hybridoma and Monoclonal GnRH Antibodies

Male BALB/C mice were immunized with 100 μg of a conjugate of synthetic GnRH and a carrier protein BSA (Bovine Serum Albumin). The conjugate was administered as a multi-site sub-cutaneous injection in an emulsion of Freund's Complete Adjuvant (Difco Labs.) Mice were bled via the infra-orbital sinus, and serum was tested for titer development via a primary binding assay. Mice were boosted with a similar conjugate emulsified in Freund's incomplete adjuvant after one month and titers again checked. The mouse with the highest positive titer was boosted with 200 μg GnRH-BSA conjugate in 200 μl saline intravenously via the tail vein. Four days later the mouse was killed by cervical dislocation and the mouse spleen cells were removed and harvested.

The spleen cells were fused with BALB/C NS-1Ag4-1 myeloma cells by incubation of the two cell types in the presence of 40% polyethylene glycol solution for 10 minutes according to the procedure developed by Kohler and Milstein.

Cells were plated onto 96-well culture plates and incubated in the presence of a restrictive growth medium consisting of RMPI 1640 medium (available from Gibco, Grand Island, N.Y.), Gentamycin 50mg/L, Glutamine 2 mM, NCTC (Gibco) 10%, glucose 4.5 gm/L, selonite 1.73 mg/L, hypoxanthine 10 mM, aminopterin 0.4 mM, thymidine 3 mM, and Fetal Bovine Serum (FBS) (Gibco) 20%.

Feeder macrophage cells were collected via mouse peritoneal lavage and were grown in tissue culture overnight to precondition the media and plastic culture ware.

The cells were fed media containing hypoxanthine, aminopterin and thymidine (HAT) every three days. At 10 days incubation viability of clones was assessed visibly and at 14 days an initial screening for antibody production was performed using a primary binding assay.

Aminopterin was removed from the culture media after four weeks and thymidine and hypoxanthine were removed one week later.

To produce ascites fluid, Balb/C mice which 7 days previously had been injected with 0.25 ml pristane (Sigma) I.P. were injected with from 100,000 to 1,000,000 cells I. P. Ascites tumors usually took 2 to 3 weeks to develop and when abdominal distention became pronounced, mice were killed and the ascites fluid collected. Cells from tissue culture and cells harvested from ascites fluid were frozen in liquid nitrogen in FBS plus 0.5% dimethyl sulfoxide (DMSO).

EXAMPLE 2

Inhibition Assay for GnRH

A competitive inhibition radioimmunoassay for the measurement of GnRH in nanogram amounts was developed. Iodinated GnRH was diluted in PBS, 0.1% gelatin to give approximately 20,000 cpm in 100 μl. Cell line ascites fluid containing USASK/DSIL-GnRH was diluted to 1:2,000,000 in PBS +0.1% gelatin. Standard concentrations of GnRH, from 1.25 ng to 320 ng/ml in doubling dilutions were formulated. Standards (0.1 ml) were incubated with antibody solution (0.1 ml) plus iodinated GnRH label (0.1 ml) overnight at 4° C. Bound label was separated via the cold ethanol precipitation (1 ml) and centrifugation. The precipitate was counted on a Micromedic automated Gamma counter. The competitive inhibition assay was used to measure unknown concentrations of GnRH as well as the basis for comparing competitive inhibition curves for GnRH with several GnRH analogues.

EXAMPLE 3.

ELISA for Allotyping of GnRH Antibodies

A triple antibody enzyme linked immunosorbant assay system (ELISA) was developed to determine the specific allotype of USASK/DSIL-GnRH. GnRH-BSA conjugate was diluted to 50 μg/nl in coating buffer ($Na_2CO_3$ 1.59 gm, $NaHCO_3$ 2.93 gm, $NaN_3$)to 96-well microtiter plates - Immulon 2, Fisher Scientific. Plates were incubated at 4° C. overnight and either used immediately or frozen for later use. Prior to use plates were warmed to room temperature and washed with distilled water. Doubling dilutions of cell supernatant from a re-cloned cell line culture of USASK/DSIL-GnRH, diluted in washing solution (0.05 M PBS, 0.05% gelatin) to a total volume of 0.1 ml were incubated in microtiter wells for 1 hour. After again washing plate with distilled water, rabbit anti-mouse allotypic antisera (Rabbit anti-mouse whole serum, -IgG1, -IgG2a, -IgG2b, -IgG3, IgM all from Miles Laboratories) at 1:1000 dilution in washing solution were incubated in wells for 1 hour and plates were again washed as before. This was followed by addition of goat anti-rabbit IgG antibodies, conjugated to horseradish peroxidase, to the wells and an additional 1 hour incubation. After a final wash 100 µl developing solution (5-amino-salicylic acid +0.002%, $H_2O_2$) was added to wells and the optical density was determined on a Tetertech Multiscan spectrophotometer at 492 nm after a 30 minute incubation.

EXAMPLE 4

Dog Passive Immunization Trial

Seven mongrel spayed dogs were passively immunized with crude mouse ascites fluid derived from cell line containing USASK/DSIL-GnRH. Ascites fluid was centrifuged at 25,000 rpm for 1 hour and the supernatant used for injections. Four dogs received a dose of 4.5 ml of ascites fluid administered intravenously at time 0, while three dogs received a dose of 0.5 nl intravenously at time 0. Blood samples were taken every 30 minutes for 4 hours prior to antiserum administration, 4 hours immediately post administration, and for additional 4 hour periods on days 1, 4 and 7 post administration. Blood samples were allowed to clot at room temperature, were centrifuged at 3000 rpm for 10 minutes and the serum collected and frozen for subsequent analysis. Serum concentrations of Luteinizing Hormone (LH) were measured using a heterologous radioimmunoassay. Serum samples (0.1 ml) were incubated with anti-ovine LH antisera (Niswender's No. 15) diluted to 1:60,000 in PBS +0.1% gelatin buffer. Iodinated ovine LH (Chloramine-T method) was diluted in PBS, 0.1% gelatin such that 0.2 ml gave about 20,000 cpm. Ovine LH (National Institute of Health) in doubling concentrations from 0.25 µg/ml to 64 µg/ml was used to generate a standard hormone inhibition curve. Second antibody precipitation was achieved using a sheep anti-rabbit IgG antisera. Assay sensitivity was to 0.5 ng LH per ml while the intra-assay coefficient of variation between assays was 10%. The titer of the USASK/DSIL GnRH was measured in the dog serum using a primary binding assay.

EXAMPLE 5

Passive Immunization in Male Rats

Young mature male rats (Sprague-Dawley, 200 gm) were injected with 0.05 ml of pooled mouse ascites fluid intraperitoneally (n=6), intravenously (n=4) or with 0.5 ml saline solution intraperitoneally (n=5). Daily blood samples were taken via tail snipping for measurement of GnRH antibody titer decay. After 10 days, several test rats had titers below an arbitrarily chosen 30% binding at 1:1000 serum dilution, and rats were re-immunized with 0.5 ml pooled ascites fluid via i.v. or i.p. routes. A similar booster was given on day 20 of the trial. Four days before the end of the experiment, female rats were housed with the males. The males ability to inseminate and impregnate the females was monitored via vaginal smears and laparotomy of females. Rats were killed on day 32 of the trial, and testes, epididymides, seminal vesicles and prostate glands were weighed and fixed in Bouin's solution for histological examination. Blood samples taken during the trial were analyzed for testosterone using a tritiated testosterone RIA system.

EXAMPLE 6

Pregnant Rat Passive Immunization Trial

Young mature female Sprague-Dawley rats (weight 250 gm) were housed with male rats of known fertility. Daily vaginal smears were taken to determine cyclicity and to check for presence of sperm cells. Day 0 of pregnancy was designated as the day that sperm was detected on the smear. Rats underwent laparotomy on either day 8 or day 9 to check for pregnancy. Anesthesia was induced using ether and maintained using 3% halothane (Somnothane, trade mark of Hoechst) with oxygen. Only pregnant animals with more than 7 implantation sites were included in subsequent trials.

Control rats (n=5) received 0.5 ml pooled nonspecific mouse serum administered intravenously via jugular injection on day 8 of pregnancy. Test rats received 0.5 ml pooled ascites fluid given intravenously via jugular injection either on day 8 (n=8) or day 9 (n=6) of pregnancy, depending on the day of laporotomy. A further group of rats having as an interperitoneal progesterone implant (1 cm in length, 10% progesterone by weight mixed in Dow-Corning medical grade elastomer resin), received 0.5 ml pooled ascites fluid intravenously on day 9 of pregnancy.

Blood samples were taken via jugular venipuncture on days 8 (or 9), 12 and 15 of pregnancy. Rats were killed or ovariectomized on day 15 of pregnancy. Ovaries and uteri were weighed and fixed in Bouin's solution for histological sectioning. Serum was analyzed for progesterone via an iodinated progesterone radioimmunoassay using rabbit anti-progesterone antisera for first antibody and preprecipitated sheep anti-rabbit IgG sera as second antibody. Progesterone standards (5 pg to 1ng) were used to generate a standard curve.

Pregnant rats were used in a trial designed to determine the minimal dose of ascites fluid required to terminate pregnancy. Female rats were laparotomized on day 9 of pregnancy and passively immunized with pooled ascites fluid containing USASK/-DSIL-GnRH given intraperitoneally. Groups of n=2 rats were given 0.4 ml, 0.2 ml, 0.1 ml or 0.05 ml ascites fluid respectively. Rats were again laparotomized on day 12 of pregnancy to determine the effect of the immunization.

RESULTS

Monoclonal Antibodies to GnRH

Figure 1:
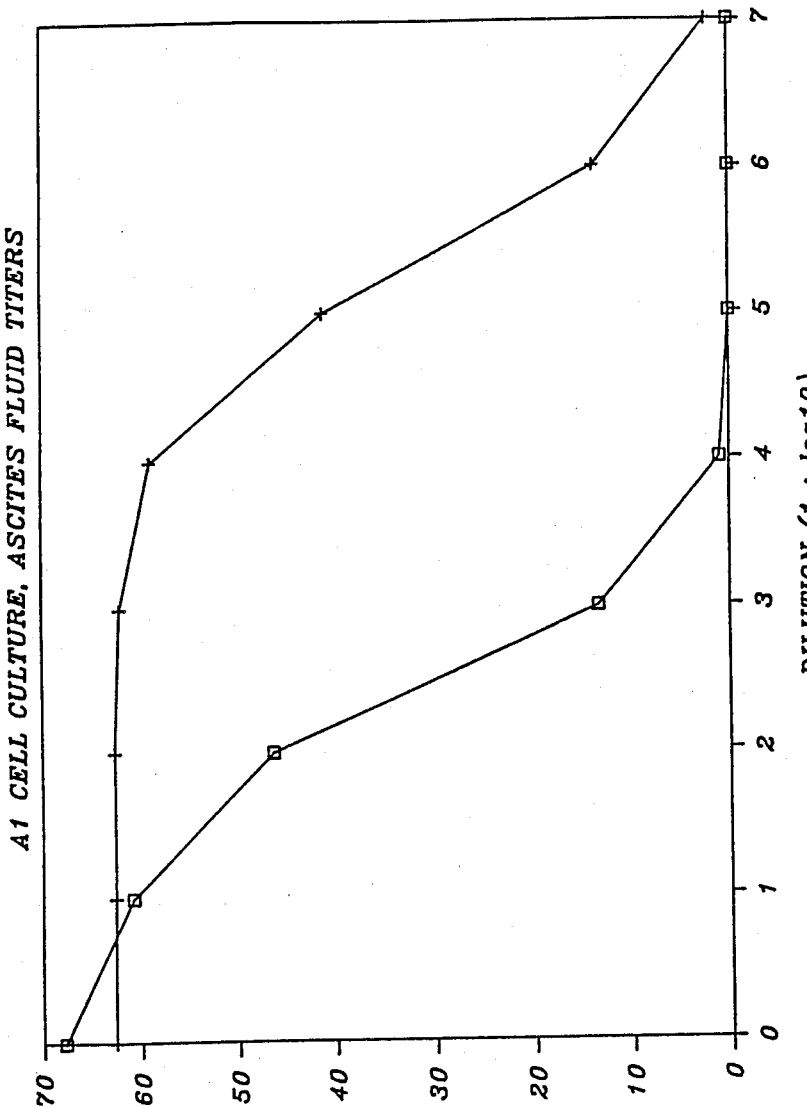
FIG. 1 shows graphically a comparison of the titer of the cell supernatant and ascites fluid for USASK/-DSIL-GnRH against $I^{125}$ GnRH.

The primary binding screening assay revealed that fluid from 11 wells showed significant binding of the GnRH label, and cells from these wells were transferred into 24-well plastic cell culture plates. 5 Cell lines subsequently lost their ability to secrete GnRH antibodies. The remaining 6 cell lines were sequentially transferred into 25 cm culture flasks, 75 cm culture flasks, and then serially recloned to check the purity of the cell line. Four cell lines were selected for passage through pristane primed BALB/C mice to generate high titer ascites fluid. One cell line, designated Hy-USASK/-DSIL-GnRH-Al, proved to be of higher titer than the others, and ascites fluid from this line was used in subsequent in vivo trials. Titers of cell supernatant and ascites fluid derived from cell line Hy-USASK/DSIL-GrNH-Al are compared in FIG. 1.

In Vitro Characterization of Monoclonal Antibodies

Figure 2:
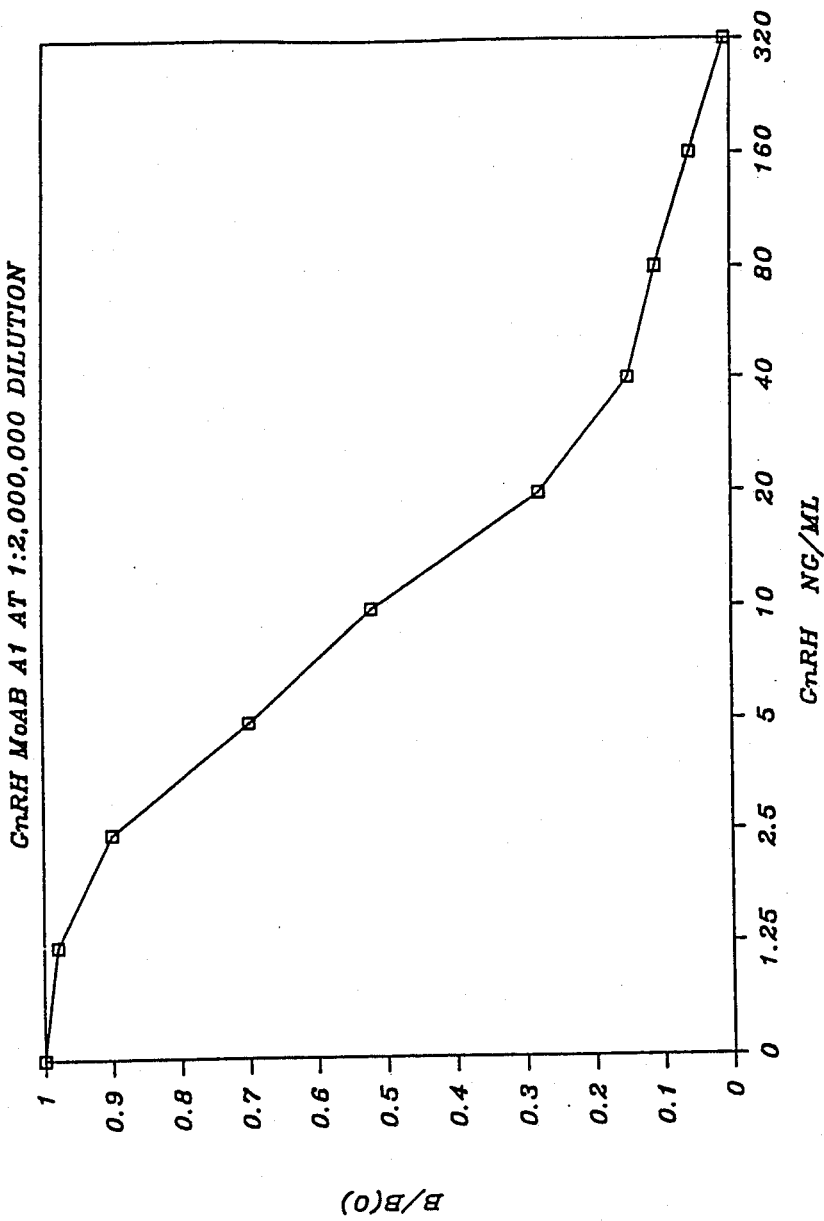
FIG. 2* shows graphically a competitive inhibition curve for USASK/DSIL-GnRH for the detection of GnRH.
Figure 3:
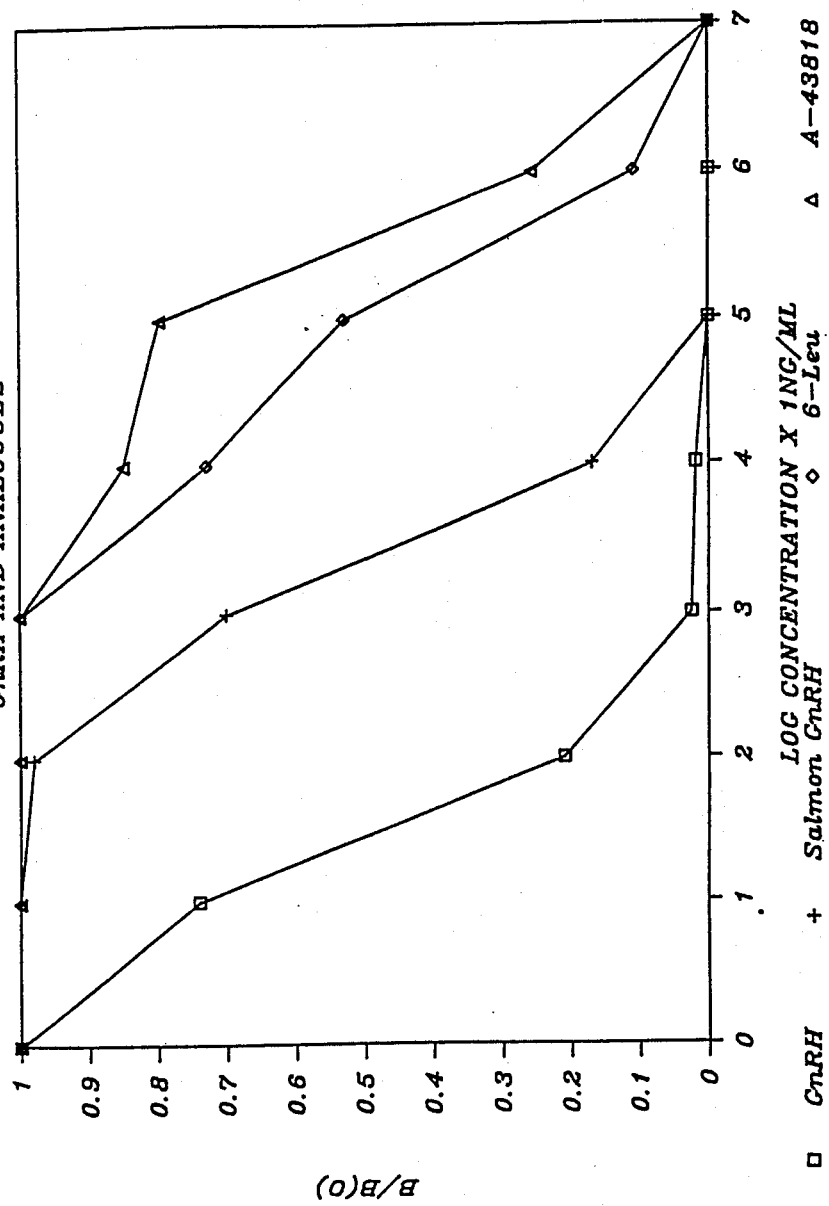
FIG. 3* shows graphically competitive inhibition curves for GnRH and GnRH analogs.

Crude ascites fluid developed from cell line Hy-USASK/DSIL-GnRH-Al was used in the development of a competitive inhibition assay for the detection of GnRH. A typical inhibition curve is shown in FIG. 2 using synthetic GnRH as standard. Similar inhibition curves were generated using salmon GnRH and other GnRH analogs, namely Salmon GnRH (Leu 6-Trp7 GnRH); 6-D-Leu GnRH; and D-leu6-Des-Gly-$NH_2^{10}$-Pro-ethylamide (A-43818), FIG. 3.

FIG. 4 shows preliminary results of the ELISA for allotype determination of USASK/DSIL-GnRH. The allotype appears to be mouse IgG1.

In Vivo Validation of USASK/DSIL-GnRH

FIGS. 5 and 6 depict LH levels of dogs immunized with 4.5 ml and 0.5 ml pooled mouse ascites fluid, respectively. Mean LH levels and pulsatile nature of LH secretion were both reduced in the high dosage dogs for up to 4 days post immunization. LH levels were unaffected in the low dosage dogs.

Mean titers of USASK/DSIL-GnRH at 1:1000 serum dilution measured by primary binding assay, are shown in FIG. 7 (A,B). Biological activity (ability to reduce LH levels) of antibodies is associated with titers greater than those developed by the low dose immunization (5% binding immediately after immunization). Biological activity is still apparent on day 4 post immunization in the high dose dogs, and corresponds with titers of at least 10% binding.

Table 1 summarizes the results from the pregnant rat immunization trial. Pooled ascites fluid (0.5 ml) was uniformly effective in terminating pregnancy when administered i.v. on day 9 of pregnancy. The same dosage was 75% effective in terminating pregnancy when administered on day 8 of pregnancy. Rats injected on day 9 of pregnancy with 0.5 ml ascites fluid while at the same time receiving a progesterone implant maintained their pregnancies. Progesterone values at days 8 or 9, 12 and 15 are shown in FIG. 8 (A,B). Termination of pregnancy corresponded with a marked decline in progesterone levels. The two rats that maintained their pregnancies when treated with ascites fluid on day 8 also maintained high progesterone levels.

Table 2 shows the results of the dose-response titration trial. A dosage of 100 μl ascites fluid was 50% effective in terminating pregnancy. Doses above this level were 100% effective while doses below this level were 0% effective in terminating pregnancy. Thus a dosage of about 0.4 ml/kg was 50% effective in terminating pregnancy.

Pregnancy termination appeared to be an all or nothing effect. In animals in which pregnancy was maintained all implantation sites seen at day 9 were still present at the end of the experiment.

The significance of the day of administration to the female rat for termination of pregnancy can be explained by reference to the sequence of ovarian secretions controlling the maintenances of gestation. From days 1 to 8 after conception the hormone prolactin is secreted, and the Lutenizing Hormone (LH) is only secreted during days 7 to 12. From day 12 onwards the placenta takes over in maintaining a milieu for development of the embryo. Thus in order to be effective in terminating pregnancy in the rat with monoclonal antibodies against GnRH, the monoclonal antibodies must be administered or be present during the period when the LH plays a prominent role in the maintenance of pregnancy.

Of course, different sequences are observed in different animals.

Long term (30 days) maintenance of USASK-GnRH titers above 30% binding of radioactive label at 1:1000 serum dilution had profound effects on male rat breeding ability, sex gland weights and morphology and serum testosterone levels. Two routes of administration of the ascites fluid, i.p. and i.v., failed to show any difference in titer development (FIG. 9).

A four day breeding challenge just prior to the termination of the experiment showed marked differences between the ability of control and test animals to inseminate and impregnate cycling female rats (Table 3).

Weights of testicles, epididyides, seminal vesicles and prostate glands in control and treatment animals are shown in FIG. 10. Testicle weights in treated animals were reduced by one third compared to that of controls, while other gland weights were reduced even further.

Testosterone values (FIG. 11) in the test animals are substantially reduced compared to control animals.

TABLE 1

Effect of USASK/DSIL-GnRH administered in 0.5 ml mouse ascites fluid injected i.v. on days 8 or 9 of pregnancy, on the maintenance of pregnancy in the rat.

| TREATMENT | NO. RATS | NO. RATS WITH VIABLE SITES DAY 15 | NO. VIABLE SITES DAY 8/9 | NO. VIABLE SITES DAY 15 | WEIGHT UTERUS MEAN + S.D., gms |
|---|---|---|---|---|---|
| CONTROL | 4 | 4 | 11 + 2.2 | 11 + 2.2 | 14.7 + 3.1 |
| TEST DAY 8 | 6 | 0 | 11.3 + 3 | 0 | 1.02 + .41 |
|  | 2 | 2 | 11.5 + 9 | 9.5 + 6.4 | 9.5 + 2.7 |
| TEST DAY 9 | 6 | 0 | 14.7 + 2.3 | 0 | .73 + .15 |
| IMPLANT | 4 | 4 | 15.3 + 1 | 15.3 + 1 | 19.3 + 2.3 |

TABLE 2

Dose titration of USASK/DSIL-GnRH in mouse ascites fluid administered via intraperitoneal injection to rats during day nine of pregnancy

| RAT NO. | VOLUME ASCITES (ul) | BODY WEIGHT (gm) | PREGNANCY (DAY 12) |
|---|---|---|---|
| M.5,M.16 | 400 | 240, 236 | −, − |
| M.3,M.4 | 200 | 244, 237 | −, − |
| M.17,M.6 | 100 | 231, 265 | −, + |

TABLE 2-continued

Dose titration of USASK/DSIL-GnRH in mouse ascites fluid administered via intraperitoneal injection to rats during day nine of pregnancy

| RAT NO. | VOLUME ASCITES (ul) | BODY WEIGHT (gm) | PREGNANCY (DAY 12) |
|---|---|---|---|
| M.8, M.13 | 50 | 251, 248 | +, + |

TABLE 3

MALE RAT CHALLENGE BREEDING TRIAL

|  | No. Males cycling | No. Females cycling | Females bred/females cycling | Pregnant/bred |
|---|---|---|---|---|
| Control | 5 | 4 | 4/4 = 100% | 3/4 = 75% |
| Test | 10 | 10 | 2/10 = 20% | 0/2 = 0% |

We claim:

1. A monoclonal antibody designated USAKS/DSIL-GnRH produced by a hybridoma deposited in ATCC under designation HB-9094 and formed by fusion of cells from a mouse myeloma line and antibody producing spleen cells from a mouse previously immunized with a source of GnRH, said monoclonal antibody having the following characteristics:
   (i) producing a short term reduced mean level of LH in female mammals of the zoological order Carnivora after passive immunization;
   (ii) producing a short term reduced pulsatile secretion of LH in female mammals of the zoological order Carnivora after passive immunization;
   (iii) being effective in passive immunization to terminate pregnancy in a female mammal of the zoological order Carnivora with an accompanying decline in progesterone levels;
   (iv) being effective in passive immunization to produce a long term reduced testosterone level in a male mammal of the zoological order Carnivora; and
   (v) being effective in passive immunization to induce infertility in a male mammal of the zoological order Carnivora.

2. A monoclonal antibody according to claim 1, which is of the mouse IgG1 allotype.

3. A monoclonal antibody according to claim 2, wherein said spleen cells are from a mouse previously immunized with GnRH conjugated to a carrier.

4. A monoclonal antibody according to claim 3, wherein said carrier is a protein.

5. A monoclonal antibody according to claim 3, wherein said carrier is bovine serum albumin.

6. A method for reducing testosterone levels in a male mammal of the zoological order Carnivora comprising passively immunizing a male mammal of the zoological order Carnivora with an effective amount of a monoclonal antibody as defined in claim 1.

7. A method for inducing infertility in a male mammal of the zoological order Carnivora comprising passively immunizing a male mammal of the zoological order Carnivora with an effective amount of a monoclonal antibody as defined in claim 1.

8. A hybridoma formed by fusion of cells from a myeloma line and spleen cells from a mouse previously immunized with a source of GnRH and being effective to produce monoclonal antibodies to GnRH effective in passive immunization of female mammals of the zoological order Carnivora to terminate pregnancy and prevent ovulation, and to effect reduced mean LH levels and reduction in pulsatile secretions of LH for a period following such passive immunization, said hybridoma being deposited in ATCC under designation HB-9094.

9. A hybridoma according to claim 8, wherein said fusion is carried out with polyethylene glycol.

10. A hybridoma according to claim 4, wherein said source of GnRH comprises GnRH conjugated to a carrier.

11. A hybridoma according to claim 10, wherein said carrier is bovine serum albumin.

12. A method of producing a hybridoma deposited in ATCC under designation HB-9094 comprising fusing cells from a mouse myeloma line and spleen cells from a mouse previously immunized with a source of GnRH and isolating said hybridoma, said hybridoma being effective to produce monoclonal antibodies to GnRH effective in passive immunization of female mammals of the zoological order Carnivora to terminate pregnancy and prevent ovulation, and to effect reduced mean LH levels and reduction in pulsatile secretions of LH for a period following such passive immunization.

13. A method according to claim 12, wherein said source of GnRH comprises GnRH conjugated to a carrier.

14. A process for producing monoclonal antibodies to GnRH effective in passive immunization of female mammals of the zoological order Carnivora to terminate pregnancy and prevent ovulation, and to effect reduced mean LH levels and reduction in pulsatile secretions of LH for a period following such passive immunization comprising:
   (a) immunizing a mouse with a source of GnRH,
   (b) removing antibody-producing spleen cells of the immune system from the immunized mouse and forming a suspension of the cells,
   (c) fusing the cells with a myeloma line,
   (d) diluting and culturing the cells from (c) comprising hybrid cells and unfused cells in separate wells in medium which will not support the unfused cells,
   (e) assaying the supernatant in the wells containing hybrid cells for the presence of antibody demonstrating a specificity to GnRH,
   (f) cloning a selected hybridoma from (e) deposited in ATCC under designation HB-9094 as a source of monoclonal antibodies to GnRH, to form a cloned hybridoma, and
   (g) producing monoclonal antibodies to GnRH from said cloned hybridoma.

15. A process for producing monoclonal antibodies to GnRH effective in passive immunization of female mammals of the zoological order Carnivora to terminate pregnancy and prevent ovulation, and to effect reduced mean LH levels and reduction in pulsatile secretions of LH for a period following such passive immunization comprising:
   (a) immunizing a mouse with a source of GnRH,
   (b) removing the spleen from said immunized mouse and forming a suspension of spleen cells,
   (c) fusing said spleen cells with a mouse myeloma line to form hybridomas and unfused cells,
   (d) diluting and culturing said hybridomas and unfused cells in separate wells in a medium which will not support the unfused cells, (e) assaying the supernatant in the wells containing hybridomas for the presence of antibody demonstrating a specificity to GnRH, (f) cloning a selected hybridoma from (e) demonstrating a specificity to GnRH to form a cloned hybridoma deposited in ATCC under designation HB-9094, and (g) producing monoclonal antibodies to GnRH from said cloned hybridoma.

16. A process according to claim 15 further including intraperitoneally administering the clonal hybridoma from (f) into mice, and harvesting ascitic fluid containing monoclonal antibodies against GnRH from said mice.

17. A process according to claim 16, wherein said source of GnRH comprises GnRH conjugated to a carrier.

18. A process according to claim 17, wherein said carrier is Bovine Serum Albumin.

19. A monoclonal antibody designated USAKS/-DSIL-GnRH produced by a hybridoma deposited in ATCC under designation HB-9094 and formed by fusion of cells from a mouse myeloma line and spleen cells from a mouse previously immunized with a source of GnRH, said monoclonal antibody being effective in passive immunization of female mammals of the zoological order Carnivora to terminate pregnancy and prevent ovulation, and to effect reduced mean LH levels and reduction in pulsatile secretions of LH for a period following such passive immunization, and having the following characteristics:

(i) an allotype mouse IgG1, (ii) a $\gamma$, heavy chain, (iii) a molecular weight of about 180,000 Daltons, (iv) a structure with 1 basic 4-peptide unit, (v) said monoclonal antibody raised as an ascites fluid tumor in the peritoneal cavity of BALB/c mice binding more than 30% of $I^{125}$ GnRH at $1:4\times10^5$ dilution of the ascites fluid in a primary binding assay, (vi) in competitive assays with $I^{125}$ GnRH, said monoclonal antibody raised as an ascites fluid tumor in the peritoneal cavity of BALB/c mice, and said ascites fluid being diluted at from $1:4\times10^5$ to $2\times10^6$, exhibiting the features:

(a) unlabelled GnRH produces 50% inhibition at about 30 mg/ml, (b) Salmon GnRH (Leu6-Trp7) produces 50% inhibition at about 2.6 $\mu$g/ml, (c) 6-D-Leu GnRH produces 50% inhibition at 100 $\mu$g/ml, (d) thyroid Releasing Hormone (TRH) produces about 50% inhibition at about 10 mg/ml, (e) LH and FSH demonstrate no competitive inhibition, (vii) said monoclonal antibody, raised as an ascites fluid tumor in the peritoneal cavity of BALB/c mice being 100% effective in terminating pregnancy at day 9 of pregnancy in female rats at a dosage of the ascites fluid of 0.8 ml/kg body weight, (viii) a minimum titre of 10% binding of said monoclonal antibody raised as an ascites fluid tumor in the peritoneal cavity of BALB/c mice, at $1:1\times10^3$ serum dilution from dog blood, being still effective in reducing LH levels in female spayed dogs, 4 days after ascites fluid injection.

20. A monoclonal antibody of GnRH produced by a hybridoma deposited in ATCC under designation HB-9094.

21. A hybridoma effective to produce monoclonal antibodies to GnRH, deposited in ATCC under designation HB-9094.

* * * * *